US012799168B2

(12) United States Patent
Lee et al.

(10) Patent No.: US 12,799,168 B2
(45) Date of Patent: Nov. 17, 2026

(54) SIGNAL SEQUENCE THAT INDUCES PROTEIN SECRETION IN INTESTINAL MICROBIOME

(71) Applicant: KOREA RESEARCH INSTITUTE OF BIOSCIENCE AND BIOTECHNOLOGY, Daejeon (KR)

(72) Inventors: Dae Hee Lee, Daejeon (KR); Seung Goo Lee, Daejeon (KR); Tae Hyun Kim, Daejeon (KR); Seong Keun Kim, Daejeon (KR); Min Jeong Choi, Daejeon (KR); Seung Gyun Woo, Daejeon (KR); Hyun Seung Lim, Daejeon (KR); Seokjin Oh, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 426 days.

(21) Appl. No.: 18/286,835

(22) PCT Filed: Apr. 5, 2022

(86) PCT No.: PCT/KR2022/004884
§ 371 (c)(1),
(2) Date: Oct. 13, 2023

(87) PCT Pub. No.: WO2022/220469
PCT Pub. Date: Oct. 20, 2022

(65) Prior Publication Data

US 2024/0190925 A1 Jun. 13, 2024

(30) Foreign Application Priority Data

Apr. 14, 2021 (KR) ........................ 10-2021-0048682

(51) Int. Cl.
*C07K 14/195* (2006.01)
*C12N 15/70* (2006.01)
*C12N 15/74* (2006.01)

(52) U.S. Cl.
CPC ............ *C07K 14/195* (2013.01); *C12N 15/70* (2013.01); *C12N 15/74* (2013.01); *C07K 2319/02* (2013.01); *C07K 2319/036* (2013.01)

(58) Field of Classification Search
None
See application file for complete search history.

(56) References Cited

U.S. PATENT DOCUMENTS

| | | | | |
|---|---|---|---|---|
| 2006/0073161 | A1 | 4/2006 | Breton | |
| 2008/0131402 | A1 | 6/2008 | Farrar et al. | |
| 2014/0056934 | A1 | 2/2014 | Blais et al. | |
| 2015/0166613 | A1 | 6/2015 | Blais et al. | |
| 2015/0175670 | A1 | 6/2015 | Blais et al. | |
| 2016/0250313 | A1 | 9/2016 | Blais et al. | |
| 2017/0029472 | A1 | 2/2017 | Blais et al. | |
| 2018/0073031 | A1* | 3/2018 | Voigt | C07K 14/28 |
| 2018/0222946 | A1 | 8/2018 | Blais et al. | |
| 2019/0099477 | A1 | 4/2019 | Stentz et al. | |
| 2019/0201457 | A1 | 7/2019 | Nguyen et al. | |
| 2019/0248841 | A1 | 8/2019 | Faridmoayer et al. | |
| 2019/0336544 | A1* | 11/2019 | Falb | A61K 31/506 |
| 2020/0331972 | A1 | 10/2020 | Blais et al. | |

FOREIGN PATENT DOCUMENTS

| | | | |
|---|---|---|---|
| KR | 10-2007-0108882 | A | 11/2007 |
| KR | 10-2013-0007991 | A | 1/2013 |
| KR | 10-2015-0072444 | A | 6/2015 |
| KR | 10-1999673 | B1 | 7/2019 |
| WO | 2018/129404 | A1 | 7/2018 |

OTHER PUBLICATIONS

J. H. Choi, et al., “Secretory and extracellular production of recombinant proteins using *Escherichia coli*”, Appl Microbiol Biotechnol, 2004, pp. 625-635, vol. 64.

Kiavash Mirzadeh, et al., “Increased production of periplasmic proteins in *Escherichia coli* by directed evolution of the translation initiation region”, Microbial Cell Factories, 2020, pp. 1-12, vol. 19, thesis No. 85.

Lian He, et al., “Intestinal probiotics *E. coli* Nissle 1917 as a targeted vehicle for delivery of p53 and Tum-5 to solid tumors for cancer therapy”, Journal of Biological Engineering, 2019, pp. 1-13, vol. 13, No. 58.

Ean-Jeong Seo, et al., “Construction of recombinant *E. coli* Nissle 1917 (EcN) strains for the expression and secretion of defensins”, International Journal of Medical Microbiology, 2012, pp. 276-287, vol. 302.

UniProtKB UniProtKB—B2UKV9 (B2UKV9_AKKM8), (Amuc_1409), 3 pages.

(Continued)

*Primary Examiner* — Michael D Burkhart
(74) *Attorney, Agent, or Firm* — Sughrue Mion, PLLC

(57) ABSTRACT

The present invention relates to a novel signal sequence peptide and a vector comprising a polynucleotide encoding same. The signal sequence peptide can induce a protein linked thereto to be secreted to the outside of a cell, and thus, when the signal sequence peptide is used or a recombinant microorganism transformed with the vector is used, the signal sequence peptide expresses a target protein and then secretes the target protein to the outside of a cell, thus enabling the target protein to exhibit the activity and function thereof.

15 Claims, 11 Drawing Sheets

Specification includes a Sequence Listing.

(56) References Cited

OTHER PUBLICATIONS

UniProtKB—Q8A5H0 (Q8A5H0_BACTN), (BT_2269), 4 pages.
UniProtKB—Q8A1C4 (Q8A1C4_BACTN), (BT_3742), 4 pages.
UniProtKB—Q89ZK9 (Q89ZK9_BACTN), (BT_4368), 4 PAGES.
UniProtKB—B2UR43 (B2UR43_AKKM8), (Amuc_1102), 3 pages.
International Search Report for PCT/KR2022/004884 dated Jul. 1, 2022 (PCT/ISA/210).
Xu Jian et al., "Protein Bacteroides thetaiotaomicron strain VPI-5482 gene BT4368 GenBank AAO79473", Database CAS [Online] May 1, 2003, XP093226651 Database accession No. 2003:234123_508632-23- 3 (1 page).
Extended European Search Report dated Mar. 27, 2025, issued in European Application No. 22788325.3.
Xu et al., Database CAS: Protein (Bacteroides thetaiotaomicron strain VPI-5482 gene BT3742), XP093226628, Database Accession No. 2003_234123_508625976_1, May 1, 2003 (1 page total).
Xu et al., "A Genomic View of the Human-*Bacteroides thetaiotaomicron* Symbiosis", Science, vol. 299, No. 5615, Mar. 28, 2003, pp. 2074-2076.
Wang et al., "Highly Efficient Extracellular Production of Recombinant Streptomyces PMF Phospholipase D in *Escherichia coli*", Catalysts, vol. 10, No. 1057, Sep. 14, 2020, pp. 1-15, doi:10.3390/catal10091057.
Partial Supplementary European Search Report issued Dec. 5, 2024 in Application No. 22788325.3.
Communication dated Apr. 13, 2026, in Korean Application No. 10-2021-0048682.
UniProtKB UniProtKB—19Q0J1 (19Q0J1_9BACE), Oct. 7, 2020, 2 pages.
UniProtKB/Swiss-Prot: 92087014, Protein yebF precursor (YEBF_ECOLI), *Escherichia coli*, (P33219), 1997, 2 pages.
Schlee, et al., "Induction of Human β-Defensin 2 by the Probiotic *Escherichia coli* Nissle 1917 Is Mediated through Flagellin", Infection and Immunity, May 2007, vol. 75, No. 5, pp. 2399-2407 (9 pages).

* cited by examiner

SIGNAL SEQUENCE THAT INDUCES PROTEIN SECRETION IN INTESTINAL MICROBIOME

CROSS REFERENCE TO RELATED APPLICATIONS

This application is a National Stage of International Application No. PCT/KR2022/004884 filed Apr. 5, 2022, claiming priority based on Korean Patent Application No. 10-2021-0048682 filed Apr. 14, 2021, the entire disclosures of which are incorporated herein by reference.

INCORPORATION BY REFERENCE OF SEQUENCE LISTING

The content of the electronically submitted sequence listing, file name: Q292609_sequence listing as filed.txt; size: 4,440 bytes; and date of creation: Oct. 12, 2022, filed herewith, is incorporated herein by reference in its entirety.

TECHNICAL FIELD

The present invention relates to a signal sequence capable of inducing a protein expressed in an intestinal microorganism to be secreted extracellularly, a vector including a polynucleotide encoding the signal sequence, and a recombinant microorganism and composition using the same.

BACKGROUND ART

Proteins that are expressed and synthesized in a cell are transported to various organelles in the cell, depending on the type and use of the protein, to serve a role according to a function of each protein. For example, the protein may be translated and synthesized in a cytoplasm and then transported to a Golgi apparatus, a peroxisome, a lysosome, etc., or transported to a membrane on a cell surface to function as a protein that constitutes a receptor, a channel, etc. In addition, a protein, such as an antibody or a hormone, may be transported outside the cell and secreted. The transportation and secretion of these proteins may be induced by a signal sequence present in some region of the protein, and an organism regulates the location of the protein by including and expressing the signal sequence in a protein sequence that is intended to be secreted outside the cell.

Meanwhile, when a recombinant microorganism is used to produce a specific protein, the signal sequence as described above may be used. When the signal sequence that induces the secretion of the protein outside the cell is expressed in a form that is linked to the protein, it is theoretically possible to secret the protein outside the cell from the microorganism, and it is expected that the protein may be obtained more easily, so research related thereto has been continuously carried out.

However, when attempting to express a protein from a different species than the one from which the signal sequence is derived, actual experiments have shown that, contrary to theoretical expectations, the protein is not successfully secreted outside the cell. In addition, as genome analysis and research continues, the genomes of various organisms and the complete sequences of proteins derived therefrom are being revealed, and as a result, parts or domains that are expected to be signal sequences in each protein have been theoretically predicted. However, there have been experimental results showing that secretion outside the cell does not occur when the corresponding sequence is actually expressed after fusion with other proteins. In this respect, it is not easy to identify sequences that function as signal sequences or to build protein expression and secretion systems in specific species based on mere theoretical predictions.

Therefore, experimental validation studies are needed to discover a novel signal sequence and show that the signal sequence can successfully induce such that the protein is transported and secreted to a desired location in a specific species. In particular, when it is possible to discover a signal sequence that is able to induce the secretion of a protein from a probiotic microbial species that provides beneficial assistance in the intestines of humans or animals, the function and effect of the protein can be exerted directly in the intestines, so there is a need for research on medicines or health functional foods that use the signal sequence.

DISCLOSURE

Technical Problem

The present invention is directed to providing a signal sequence capable of secreting a protein expressed in a microorganism of *Escherichia coli* or *Bacteroides* that is viable in the intestine and capable of functioning as a beneficial bacterium, and a fusion protein of the signal sequence and a secretion targeted protein.

In addition, the present invention is directed to providing a vector for introducing the signal sequence.

In addition, the present invention is directed to providing a recombinant microorganism capable of expressing a protein linked to the signal sequence.

In addition, the present invention is directed to providing a method of manufacturing a protein from a microorganism, in which the protein is capable of being transported outside a cell of the microorganism.

In addition, the present invention is directed to providing a composition that enables a protein to be secreted outside a cell to function in the intestine.

Technical Solution

It is one aspect of the present invention for achieving the above objects to provide a signal sequence peptide including any one selected from the group consisting of amino acid sequences of SEQ ID NO: 1 and SEQ ID NO: 2.

It is another aspect of the present invention to provide a fusion protein including the signal sequence peptide and a secretion targeted protein.

It is still another aspect of the present invention for achieving the above objects to provide a vector including a polynucleotide configured to encode a signal sequence including one selected from the group consisting of amino acid sequences of SEQ ID NO: 1, SEQ ID NO: 2, SEQ ID NO: 3, SEQ ID NO: 4, and SEQ ID NO: 5.

It is still another aspect of the present invention for achieving the above objects to provide a recombinant microorganism transformed with the vector.

It is still another aspect of the present invention for achieving the above objects to provide a method of manufacturing a protein, including inducing expression of a protein from the recombinant microorganism.

It is yet another aspect of the present invention for achieving the above objects to provide a composition including a recombinant microorganism transformed with the vector.

Advantageous Effects

A signal sequence peptide of the present invention can induce a protein linked thereto to be secreted outside a cell, and in particular, has an effect of inducing extracellular secretion of the protein expressed in *E. coli*, a microorganism of *Bacteroides* genus, or the like, which is viable in the intestine.

Therefore, a vector including a polynucleotide encoding a protein including the signal sequence peptide of the present invention, and a recombinant microorganism transformed with the vector, can be used to secrete the protein to be expressed outside the cell, and a composition including the recombinant microorganism can be used for various purposes, depending on the function and activity exhibited by the protein. In particular, by using the recombinant microorganism that is viable in the intestine, a target protein can be continuously secreted in the intestine, thus exhibiting the function of the protein without crushing the cell.

However, the effects of the present invention are not limited to the aforementioned effects, and other effects, which are not mentioned above, will be clearly understood by those skilled in the art from the following description.

MODE FOR DISCLOSURE

Figure 1:
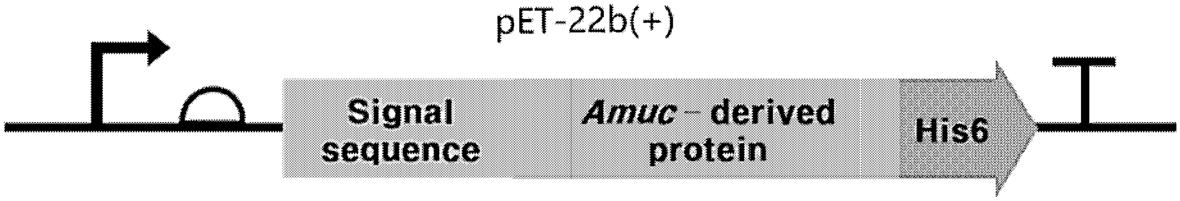
FIG. 1 is a view illustrating a configuration of a vector for transformation of *E. coli* Nissle 1917 strain, in which the vector includes a polynucleotide encoding a protein derived from *Akkermansia muciniphila* (Amuc-derived protein), a polynucleotide encoding a His6 tag, and a polynucleotide encoding a signal sequence peptide.

Hereinafter, the present invention will be described in detail.

1. Novel Signal Sequence Peptide and Fusion Protein Linked Thereto

It is one aspect of the present invention to provide a novel signal sequence peptide.

The signal sequence peptide may include any one selected from the group consisting of amino acid sequences of SEQ ID NO: 1 and SEQ ID NO: 2.

In addition, the signal sequence peptide may include any one selected from the group consisting of amino acid sequences of SEQ ID NO: 3, SEQ ID NO: 4, and SEQ ID NO: 5.

The signal sequence peptide may include a variant peptide having a different sequence by deletion, insertion, substitution, or combination thereof of amino acid residues, or may be in the form of a protein fragment having the same function, to the extent that a function of any one selected from the group consisting of the amino acid sequences of SEQ ID NO: 1, SEQ ID NO: 2, SEQ ID NO: 3, SEQ ID NO: 4, and SEQ ID NO: 5 described above is not affected. Amino acid modifications at a protein and peptide level are known in the art of the present invention, and in some cases may be phosphorylation, sulfation, acrylation, glycosylation, methylation, farnesylation, and the like, as long as the activity is not entirely changed by the inclusion of any one selected from the group consisting of amino acid sequences of SEQ ID NO: 1, SEQ ID NO: 2, SEQ ID NO: 3, SEQ ID NO: 4 and SEQ ID NO: 5. Therefore, the signal sequence peptide includes any one selected from the group consisting of the amino acid sequences of SEQ ID NO: 1, SEQ ID NO: 2, SEQ ID NO: 3, SEQ ID NO: 4, and SEQ ID NO: 5, as well as a peptide having an amino acid sequence substantially identical thereto, or a variant thereof. The peptide having the substantially identical amino acid sequence, may be a peptide including any one selected from the group consisting of an amino acid sequences of SEQ ID NO: 1, SEQ ID NO: 2, SEQ ID NO: 3, SEQ ID NO: 4, and SEQ ID NO: 5, and an amino acid sequence having homology of 90% or more, 91% or more, 92% or more, 93% or more, 94% or more, 95% or more, 96% or more, 97% or more, 98% or more, 99% or more, or 99.5% or more, but is not limited thereto, as long as the peptide includes a signal sequence comprising any one selected from the group consisting of the amino acid sequences of SEQ ID NO: 1, SEQ ID NO: 2, SEQ ID NO: 3, SEQ ID NO: 4, and SEQ ID NO: 5, and a sequence having homology of 90% or more of the amino acid sequence, while having the same activity, which is included in the scope of the present invention.

The signal sequence peptide may be one that induces extracellular secretion of a protein linked to the peptide, in a microbial strain that is viable in the intestine. The microbial strain viable in the intestine may be a strain of *Escherichia coli* or *Bacteroides*. Specifically, the *E. coli* may be an *E. coli* Nissle strain, and more specifically, the *E. coli* may be an *E. coli* Nissle 1917 strain. The strain of the genus *Bacteroides* may be a strain of *Bacteroides thetaiotaomicron.*

The signal sequence peptide may function in the form linked to a protein, and when in the form linked to the protein, the protein may be transported outside the cell.

It is another aspect of the present invention to provide a fusion protein that is capable of being secreted outside the cell.

The fusion protein includes the signal sequence peptide and the secretion targeted protein.

The term "fusion protein" in the present invention means that the signal sequence peptide and the secretion targeted protein included therein are physically linked together without losing their respective original functions. The signal sequence peptide of the present invention functions to transport the secretion targeted protein physically linked thereto outside the cell, such that the fusion protein of the present invention may be secreted outside the cell.

The secretion targeted protein is any protein or polypeptide other than the signal sequence peptide, and is not limited thereto. For example, the secretion targeted protein may be, but is not limited to, an enzyme, a hormone, a cytokine, an antibody, a protein adjuvant, or a fragment having activity thereof.

The signal sequence peptide may be directly linked to one or more of the amino acids constituting the secretion targeting protein, or may be linked through a linker.

The linker may be any material capable of physically linking the signal sequence peptide to the secretion targeted protein without affecting the extracellular secretion activity of the signal sequence peptide and without affecting the activity of the secretion targeted protein. For example, the linker may be a linker peptide of any amino acid sequence, and may be a peptide consisting of 1 to 30, 1 to 20, 2 to 15, 3 to 10, or 4 to 8 amino acids, but is not limited thereto.

All or a portion of the signal sequence peptide may be isolated from the fusion protein after the fusion protein has been transported and secreted outside the cell. For example, the signal sequence peptide may be separated from the fusion protein by cleavage at the linker portion of the secretion targeted protein or by removal of the linker.

The signal sequence peptide may be, but is not limited to, one that is linked to an N-terminal, a C-terminal, or a central hydrophobic region of the secretion targeted protein.

The fusion protein including the signal sequence peptide of the present invention may be induced to be transported outside the cell. Therefore, the signal sequence peptide of the present invention may be beneficially used when the protein expressed in the cell is intended to be secreted outside the cell. In particular, the signal sequence peptide of the present invention can induce the secretion of protein from probiotics such as *E. coli* or microorganisms of the genus *Bacteroides*, which can survive in the intestine and exhibit beneficial effects on a human body. Therefore, the signal sequence of the present invention can be used to continuously and efficiently secrete a target protein in the intestine of a human or animal.

2. Polynucleotide Encoding Signal Sequence and Expression Vector Including the Same.

It is another aspect of the present invention to provide a polynucleotide encoding the signal sequence.

The polynucleotide encoding the signal sequence may include all of the encoded base sequence such that, through transcription and translation, a peptide substantially identical to the signal sequence may be produced. For example, when there are a plurality of base sequences encoding a single amino acid, any one of these base sequences may be selected and included, and there may be various combinations of base sequences that are capable of encoding each of the amino acids constituting the signal sequence. The polynucleotide encoding the signal sequence may include any one selected from the group consisting of base sequences of SEQ ID NO: 6, SEQ ID NO: 7, SEQ ID NO: 8, SEQ ID NO: 9, and SEQ ID NO: 10. However, the base sequence of the polynucleotide may be subjected to various modifications in an encoding region without altering the amino acid sequence of the signal sequence peptide or a variant thereof, and the signal sequence peptide of the present invention may be expressed from a polynucleotide including a base sequence substantially identical to any one selected from the group consisting of the base sequences of SEQ ID NO: 6, SEQ ID NO: 7, SEQ ID NO: 8, SEQ ID NO: 9, and SEQ ID NO: 10. The substantially identical base sequence means a nucleic acid sequence having homology of 90% or more, 91% or more, 92% or more, 93% or more, 94% or more, 95% or more, 96% or more, 97% or more, 98% or more, 99% or more, or 99.5% or more, but is not limited thereto.

In addition, it is still another aspect of the present invention to provide a vector including a polynucleotide encoding the signal sequence.

The vector may be an expression vector for expressing a protein, and more specifically, the vector may be for extracellular secretion by expressing a fusion protein including the signal sequence and secretion targeted protein in a microbial strain viable in the intestine.

The vector may further include a cloning site for cloning a polynucleotide encoding the secretion targeted protein, or may further include a polynucleotide encoding the secretion targeted protein.

The secretion targeted protein is any protein or polypeptide other than the signal sequence peptide, and is not limited thereto. For example, the protein may be, but is not limited to, an enzyme, a hormone, a cytokine, an antibody, a protein adjuvant, or a fragment having activity thereof.

The secretion targeted protein may have an activity that may improve human or animal health or prevent, treat, or ameliorate a disease, and more particularly, the secretion targeted protein may have an activity that may have a direct beneficial effect on a human or animal in the intestine, or may have an activity that may have a beneficial effect on the microbial flora of the intestine. Accordingly, the vectors of the present invention may be used to express the secretion targeted protein having the above activity, and as expressed in the form of a fusion protein with the signal sequence peptide, the secretion targeted protein may be secreted outside the cell.

The cloning site is a site at which a polynucleotide encoding the secretion targeted protein to be expressed through the vector of the present invention is inserted, and may include one or more restriction enzyme sites. The restriction enzyme sites within the cloning site may be variously configured depending on the purpose.

The vector of the present invention may include both a polynucleotide encoding the signal sequence and a polynucleotide encoding the secretion targeted protein, in which the signal sequence and the secretion targeted protein are expressed in the form of a fusion protein, such that the fusion protein is secreted outside the cell. Where the signal sequence and the secretion targeted protein are linked by a linker peptide, the vector of the present invention may further include a polynucleotide encoding the linker peptide. For example, a polynucleotide encoding the signal sequence peptide, a polynucleotide encoding the linker peptide, and a polynucleotide encoding the secretion targeting protein may be included in the vector of the present invention in a linked form.

The microbial strain viable in the intestine may be a microbial strain of *Escherichia coli* or *Bacteroides*. Specifically, the *E. coli* may be an *E. coli* Nissle strain, and more specifically, the *E. coli* may be an *E. coli* Nissle 1917 strain. The strain of the genus *Bacteroides* may be a strain of *Bacteroides thetaiotaomicron.*

The vector may further include a promoter operably linked to a polynucleotide encoding the secretion targeted protein. Specifically, the promoter may be operably linked to a polynucleotide encoding the fusion protein including the signal sequence peptide and the secretion targeted protein.

The promoter means a DNA sequence capable of regulating the transcription of the polynucleotide into mRNA, in which the promoter may be suitably selected according to the type of microorganism in which the vector is transformed. The promoter may be upstream of the polynucleotide and may include a site to which an RNA polymerase or other transcription factor may specifically bind. The promoter may be a constitutive promoter or an inducible promoter. When the promoter is a constitutive promoter, transcription of the polynucleotide operably linked thereto may be initiated without the need for a specific stimulus. When the promoter is an inducible promoter, transcription of the polynucleotide may be initiated only when a specific stimulus is given, for example, a ligand (chemical, etc.), heat shock, etc. Specifically, the promoter may be such that the promoter initiates transcription in the presence of IPTG, in which case a protein encoded by the polynucleotide may be expressed when the recombinant microorganism in which the vector is transformed is treated with the IPTG.

The promoter may be a *Bacteroides thetaiotaomicron*-derived $P_{BT1311}$ promoter or a *Bacteroides fragilis*-infecting phage-derived $P_{BfP1E6}$ promoter. When the promoter included in the vector of the present invention is the $P_{BT1311}$ promoter or the $P_{BfP1E6}$ promoter, the vector may be for transforming a strain of *Bacteroides thetaiotaomicron* as a host microorganism. The $P_{BfP1E6}$ promoter may be more efficient in initiating transcription than the $P_{BT1311}$ promoter, but the promoter may be suitably selected and used depending on the type of signal sequence used and the type of protein to be expressed.

The vector may further include configurations that may be included in a conventional expression vector used for the purpose of expressing a protein, and may further include, for example, a replication origin sequence, a restriction enzyme cleavage site, a ribosome binding site, an operator sequence, a terminator sequence, an enhancer sequence, an initiation codon, a termination codon, a polyadenylation signal, and the like. In addition, the vector may further include a selection marker gene to enable confirmation and selection of whether the vector has been properly transformed into a host microorganism, and the selection gene may be, but is not limited to, an antibiotic resistance gene, a gene associated with a chromogenic response, and the like.

The vector may be a plasmid vector, a cosmid vector, a bacteriophage vector, or a viral vector, for example, the vector may be a pET-22b(+) vector or a pMM553 vector, but is not limited thereto.

In a specific experimental example of the present invention, a vector including signal sequences of SEQ ID NO: 3, SEQ ID NO: 4, or SEQ ID NO: 5 of the present invention and a polynucleotide encoding a foreign protein was manufactured. Further, the vector was transformed into the *E. coli* Nissle 1917 strain and the expression of the protein was induced. Then, the protein in the culture solution was analyzed by SDS-PAGE and western blotting, and it was confirmed that the foreign protein combined with the signal sequence of SEQ ID NO: 3, SEQ ID NO: 4, or SEQ ID NO: 5 expressed from the above vector was contained in the culture solution, thus confirming that the vector using the signal sequence peptide of the present invention is capable of producing a protein that is capable of being transported outside the cell of the *E. coli* Nissle 1917 strain.

In another specific experimental example of the present invention, a vector including signal sequences of SEQ ID NO: 1, SEQ ID NO: 2, or SEQ ID NO: 3 of the present invention and a polynucleotide encoding a foreign protein was manufactured. Further, the vector was transformed into the *Bacteroides thetaiotaomicron* strain and the expression of the protein was induced. Then, the protein in the culture solution was analyzed by SDS-PAGE and western blotting, and it was confirmed that the foreign protein combined with the signal sequence of SEQ ID NO: 1, SEQ ID NO: 2, or SEQ ID NO: 3 expressed from the above vector was contained in the culture solution, thus confirming that the vector using the signal sequence peptide of the present invention is capable of producing a protein that is capable of being transported outside the cell of the *Bacteroides thetaiotaomicron* strain.

3. Recombinant Microorganism with Enhanced Protein Secretion Capability and Method of Manufacturing Protein Using the Same It is still another aspect of the present invention to provide a recombinant microorganism with enhanced protein secretion capability and a method of manufacturing a protein using the recombinant microorganism.

The recombinant microorganism is transformed with the vector of the present invention.

The description of the vector, for example, the polynucleotide, signal sequence peptide, secretion targeting protein, effect, use, etc. contained in the vector, is the same as described in "2. Polynucleotide encoding signal sequence and expression vector including the same" above.

The recombinant microorganism may be viable in the intestine. Specifically, the recombinant microorganism may be one that is capable of exhibiting physiological activity upon prolonged residence in the intestine, and more specifically, the recombinant microorganism may be one that is capable of expressing and secreting a protein in the intestine. The recombinant microorganism may be one that is dominant in the intestine.

The recombinant microorganism may be a transformation of the vector into a microbial strain that is viable in the intestine and capable of functioning as a probiotic, which may have a beneficial effect on the human or animal health, and may be a transformation of the vector into a microorganism of *Escherichia coli* or *Bacteroides*. Specifically, the *E. coli* may be an *E. coli* Nissle strain, and more specifically, the *E. coli* may be an *E. coli* Nissle 1917 strain. The strain of the genus *Bacteroides* may be a strain of *Bacteroides thetaiotaomicron.*

The recombinant microorganism may be one that has been transformed with the vector according to a transformation method conventionally used in the art. The transformation may be in a state in which the protein encoded by the vector is expressed in the recombinant microorganism, and the protein is expressed by insertion, integration of the polynucleotide included in the vector into the genome of the recombinant microorganism, or the protein is expressed from the polynucleotide included in the vector in the cytoplasm of the recombinant microorganism. Specifically, the transformation may be achieved by, but is not limited to, methods such as electroporation, calcium phosphate ($CaPO_4$) precipitation, calcium chloride ($CaCl_2$)) precipitation, and the like.

The recombinant microorganism, upon transformation with the vector, may express the signal sequence peptide and secretion targeting protein encoded by the polynucleotide contained in the vector, and the protein expressed in the form described above may be transported, expelled, or secreted outside the recombinant microorganism. Therefore, the recombinant microorganism of the present invention can not only produce a target protein to be expressed, but can also secrete the target protein externally, so that the protein can be obtained without difficulty even without crushing the recombinant microorganism cell. In addition, since the recombinant microorganism secretes the protein externally by itself, it has an advantage in that the activity, effect, and function of the protein can be expected immediately without taking any other measures. More specifically, when the recombinant microorganism is viable in the intestine and capable of expressing and producing a protein in the intestine, ingesting or introducing the recombinant microorganism into the intestine can achieve the desired effect in the intestine, as the recombinant microorganism can continuously produce the protein in the intestine and secrete the protein externally.

The method of manufacturing a protein according to the present invention, includes a step of inducing expression of the protein in the recombinant microorganism.

The step of inducing the expression of the protein may be simply culturing the recombinant microorganism, or applying a specific stimulus to induce the expression of the protein. When the vector transformed into the recombinant microorganism is constitutively to express the protein, then the only simple culturing of the recombinant microorganism may result in the expression of the protein and the secretion of the protein outside the cell. When the vector transformed into the recombinant microorganism is to express a protein under the control of an inducible promoter, the expression of the protein may be induced by applying a specific stimulus depending on the type of promoter, for example, a ligand (chemical material, etc.), a heat shock, etc. For example, the step of inducing expression of the protein may include a step of treating the culture solution of the recombinant microorganism with IPTG.

The method of manufacturing the protein may further include a step of isolating or purifying the protein expressed from the culture solution. The method of isolating and purifying the protein may be used without limitation as long as the method is conventionally used in the art, and a method that does not impair the structure, function, or activity of the protein may be used.

The method of manufacturing the protein may further include a step of removing the signal sequence peptide from the expressed protein. A method for removing the signal sequence peptide may be appropriately selected depending on how and in what form the signal sequence peptide is linked to the protein, for example, the signal sequence peptide may be removed by treating with an enzyme having an activity to cleave the linker or the signal sequence peptide.

4. Composition for Expressing Protein in the Intestine

It is still another aspect of the present invention to provide a composition including a recombinant microorganism transformed with the vector.

The description of the vector, for example, the polynucleotide, signal sequence peptide, secretion targeting protein, effect, use, etc. contained in the vector, is the same as described in "2. Polynucleotide encoding signal sequence and expression vector including the same" above. In addition, the description of the recombinant microorganism is the same as that described in "3. Recombinant microorganism with enhanced protein secretion capability and method of manufacturing protein using the same" above.

The recombinant microorganism may be a microorganism that is viable in the intestine and capable of functioning as a probiotic, which may have a beneficial effect on the human or animal health, and may be a transformation of the vector into a microorganism of *Escherichia coli* or *Bacteroides*. Specifically, the *E. coli* may be an *E. coli* Nissle strain, and more specifically, the *E. coli* may be an *E. coli* Nissle 1917 strain. The strain of the genus *Bacteroides* may be a strain of *Bacteroides thetaiotaomicron*.

The recombinant microorganism included in the composition of the present invention includes the vector that includes a polynucleotide encoding the signal sequence peptide of the present invention, and in which the signal sequence peptide is capable of inducing secretion of the secretion targeted protein linked thereto outside the cell, and in which the composition of the present invention can cause the recombinant microorganism to produce the secretion targeted protein and cause a protein to be secreted outside the recombinant microorganism cell.

The composition may be a composition for expressing a protein in the intestine. Specifically, the composition may be a composition for expressing a protein in the intestine, and for enabling the protein to be present in the intestine by transporting, expelling, or secreting the protein outside the cell of the recombinant microorganism (into the intestinal space). Accordingly, the composition may enable the continuous production of the protein in the intestine, and may also enable the produced protein to immediately exhibit the activity, effect, or function thereof.

That is, the composition of the present invention may have a variety of uses, depending on the type of protein that is capable of being expressed and secreted by the recombinant microorganisms included therein. Specifically, the composition may be used for improving health, preventing, treating, or ameliorating a disease, and for controlling and improving the flora of the intestinal microbiota.

For example, where the protein is a protein that exhibits a pharmacologic effect on a specific disease, the composition of the present invention may be a pharmaceutical composition for the prevention or treatment of the disease, or a health functional food composition for the prevention or amelioration of the specific disease. In addition, when the protein is a cytokine, the composition of the present invention may be an immune-enhancing composition. However, the uses of the composition of the present invention are not limited thereto, and any use that may be used in accordance with the activity and function that may be exhibited by the protein expressed and secreted by the recombinant microorganism contained in the composition of the present invention falls within the scope of protection of the present invention.

The composition of the present invention may further include a cryoprotectant. The cryoprotectant may be at least one selected from the group consisting of, but is not limited to, skim milk powder, maltodextrin, dextrin, trehalose, maltose, lactose, mannitol, cyclodextrin, glycerol, and honey, and may include any agent capable of preventing the recombinant microorganism from being damaged or killed in the process of freeze-drying the composition.

When the composition includes a cryoprotectant, the composition may be used in the form of a freeze-dried product, such as a powder, which has an advantage in terms of formulation, packaging, storage, and the like, and allows for long-term preservation of the recombinant microbial strain included therein.

The composition may further include a medium component in which the recombinant microorganism included therein may grow. The medium component may include, but is not limited to, a component such as glucose, yeast extract, proteuspeptone, polysorbate 80, ammonium citrate, magnesium sulfate, dipotassium phosphate, or sodium acetate, and may include any component without limitation that may assist in the growth of the recombinant microbial strain.

The composition may not include any microorganism other than the recombinant microorganism of the present invention. To eliminate microorganisms other than the recombinant microorganism, the composition may be manufactured by culturing the recombinant microbial strain in a sterilized culture medium.

The composition of the present invention may be a health functional food composition or a pharmaceutical composition.

When the composition of the present invention is used as the food functional food composition, the type of the food may be a dairy product, including meat, sausages, bread, chocolate, candy, snacks, cookies, pizza, ramen, other noodles, chewing gum, ice cream, etc., and various soups, sodas, teas, beverages, alcoholic beverages, vitamin supplements, etc. The food product includes all foods in the conventional sense, for example, may be one in which the recombinant microorganism that are an active ingredient included in the composition are not destroyed or lose the function, during the processing or cooking of the food.

The health functional food is a food product with high medical and health effects that has been processed to efficiently exhibit bioregulatory functions in addition to nutrition provision, which can achieve useful effects for health purposes such as nutrient regulation or physiological action on the structure and function of the human body. The health functional food may be manufactured by a method conventionally used in the art of the present invention, and may be manufactured by adding raw materials and ingredients that are conventionally added in the art. In addition, the formulation of the health functional food may be manufactured in various forms of formulation without limitation as long as the formulation is recognized as a health functional food. Unlike general pharmaceuticals, since the raw materials of the health functional food comes from food, there are advantages of not having side effects that may occur when taking pharmaceuticals for a long period of time and of being highly portable. Therefore, the formulation of the dietary supplement can be used simultaneously with or independently of an agent for treatment before or after the onset of a disease that can be prevented or ameliorated depending on the function of the expressed and secreted protein. The health functional food includes health food that has an active health maintenance or enhancement effect compared to ordinary food, and health supplement food for health supplement purposes, and in some cases, the terms health functional food, health food, and health supplement food may be used interchangeably.

In the health functional food, the active ingredient (the recombinant microorganism of the present invention) may be added to the food as is or used in combination with other foods or food ingredients, and may be used as appropriate according to conventional methods. The amount of mixing of the active ingredient may be suitably determined according to the purpose of use thereof. The active ingredient may be included in the health functional food in various amounts as long as it has an effect on the expression and secretion of the protein. However, in case of long-term ingestion for health and hygiene purposes or for health control purposes, the amount may be below the range described above. In addition to including the active ingredient, the health functional food may include, without limitation, other ingredients as essential ingredients. For example, the active ingredient may include a variety of flavorings or natural carbohydrates as an additional ingredient, like a conventional beverage. Examples of the natural carbohydrate may be a monosaccharide, for example, glucose, fructose, etc., a disaccharide, for example, maltose, sucrose, etc., and a polysaccharide, for example, a conventional sugar, such as dextrin, cyclodextrin, etc., and a sugar alcohol, such as xylitol, sorbitol, erythritol, etc. As flavoring agents other than those described above, natural flavoring agents (thaumatin, stevia extract (e.g., rebaudioside A, glycyrrhizin, etc.)) and synthetic flavoring agents (saccharin, aspartame, etc.) may be advantageously used. The proportion of the natural carbohydrate may be suitably determined by the selection of one of ordinary skill in the art.

The health functional food may include various nutrients, vitamins, minerals (electrolytes), flavoring agents such as synthetic flavoring agents and natural flavoring agents, colorants and binders (cheese, chocolate, etc.), a pectic acid and salts thereof, an alginic acid and salts thereof, organic acids, protective colloidal thickeners, pH adjusters, stabilizers, preservatives, glycerin, alcohol, carbonation agents used in carbonated beverages, and the like. These ingredients may be used independently or in combination, and the proportions of these additives may be suitably selected by one of ordinary skill in the art.

When the composition of the present invention is used as a pharmaceutical composition, the pharmaceutical composition may be for the prevention or treatment of a disease that may be prevented or treated by a protein expressed or secreted by the recombinant microorganism.

The composition may be administered in combination with one or more active ingredients exhibiting the same or similar function. For administration, one or more additional acceptable carriers may be included, according to a method that can be readily practiced by one of ordinary skill in the art to which the present invention belongs. The meaning of "acceptable" above is that the activity of the active ingredient (the recombinant microorganism of the present invention) is not inhibited and there is no more than adaptable toxicity in the subject of application (prescription). The term "carrier" above is defined as a compound that facilitates the addition of a compound into a cell or tissue. The composition may be manufactured in unit dose form by formulating with a carrier and/or an excipient, or by introducing into a multi-dose container, and may further include a dispersant or a stabilizing agent. In addition, the active ingredient included in the composition may be carried in a carrier such as colloidal suspension, powders, a saline solution, lipids, liposomes, microspheres, or nano-spherical particles. The active ingredient may form a complex with or be associated with the carrier, and may be transported in vivo using a transport system known in the art to which the present invention belongs, such as lipids, liposomes, microparticles, gold, nanoparticles, polymers, condensation reactants, polysaccharides, polyamino acids, dendrimers, saponins, adsorption enhancers, or fatty acids. In addition, the carrier may include, but is not limited to, lactose, dextrose, sucrose, sorbitol, mannitol, starch, acacia, rubber, calcium phosphate, alginate, gelatin, calcium silicate, microcrystalline cellulose, polyvinyl pyrrolidone, cellulose, water, syrup, methyl cellulose, methylhydroxybenzoate, propyl hydroxybenzoate, talc, magnesium stearate, and mineral oils that are commonly used in formulation. Further, in addition to the above ingredients, lubricants, wetting agents, sweeteners, flavoring agents, emulsifiers, suspending agents, preservatives, and the like may be further included. The carrier may use a saline solution, sterile water, a Ringer's solution, a buffered saline solution, a dextrose solution, a maltodextrin solution, glycerol, ethanol, and a mixture of one or more components thereof, and other conventional additives such as antioxidants, buffers, bacteriostatic agents, etc. may be added as necessary.

When used pharmaceutically, the composition of the present invention may be administered in a variety of formulations, both oral and parenteral, in actual clinical administration, and when formulated, may be prepared using commonly used diluents or excipients such as fillers, bulking agents, binders, wetting agents, disintegrating agents, surfactants, and the like. Solid formulations for oral administration include tablets, pills, acidic formulations, granules, capsules, and the like, which are prepared by mixing the herbal extract or herbal ferment with at least one excipient, such as starch, calcium carbonate, sucrose or lactose, gelatin, and the like. In addition to a simple excipient, lubricants such as magnesium stearate talc are also used. The acidic agent may be prepared by simply mixing the active ingredient of the present invention with a suitable pharmaceutically acceptable carrier such as lactose, starch, microcrystalline cellulose, etc. The granule may be prepared by mixing the active ingredient of the present invention, a pharmaceutically acceptable suitable carrier, and a pharmaceutically acceptable suitable binder, such as polyvinylpyrrolidone and hydroxypropyl cellulose, and then using a wet granulation method that uses a solvent such as water, ethanol, and isopropanol, or a dry granulation method that uses compression forces. The tablet may also be prepared by mixing the granule with a suitable pharmaceutically acceptable active agent, such as magnesium stearate, and then tableting using a tableting machine. Liquid formulations for oral administration include suspension, oral liquid, emulsion, syrup, and the like, and may include a variety of excipients, such as a wetting agent, a sweetener, a flavoring agent, and a preservative in addition to the commonly used simple diluents of water and liquid paraffin. Formulations for parenteral administration include a sterile aqueous solution, a non-aqueous agent, suspension, emulsion, a freeze-dried agent, and suppository. As the non-aqueous agent and suspension, propylene glycol, polyethylene glycol, vegetable oils such as olive oil, and injectable esters such as ethylolate, and the like may be used. As the base of the suppository, witepsol, macrogol, twin 61, cacao butter, laurinol, glycerol, gelatin, and the like may be used.

When the composition of the present invention is used pharmaceutically, the active ingredient (the recombinant microorganism of the present invention) may be administered with oral, injection (e.g., intramuscular, intraperitoneal, intravenous, infusion, subcutaneous, or implant), inhalation, nasal, vaginal, rectal, sublingual, transdermal, or topical agents, depending on the disease to be prevented, ameliorated, or treated and the condition of the individual, but the administration is not limited thereto. Depending on the route of administration, the composition may be formulated in a suitable dosage unit formulation that includes conventionally used, non-toxic, pharmaceutically acceptable carriers, excipients, and vehicles. The amount of recombinant microorganism that is the active ingredient in the above administration may have a wide range depending on a patient's weight, age, gender, health state, diet, time of administration, method of administration, excretion rate, target site, severity of the disease, and the like. The active ingredient in the composition may be included at a concentration of 30 μM or more, for example 32 μM or more, 35 μM or more, 37 UM or more, or 40 μM or more. In addition, the active ingredient may be contained in an amount of the range consisting of one lower limit selected from 0.05 mg, 0.1 mg, 0.15 mg, 0.2 mg, 0.3 mg, 0.5 mg, 1 mg, 2 mg, 3 mg, 5 mg, 10 mg, 20 mg, 30 mg, 50 mg, and 100 mg and/or one upper limit selected from 500 mg, 450 mg, 400 mg, 350 mg, 320 mg, 300 mg, 280 mg, 250 mg, 200 mg, 150 mg and 100 mg, for example, may be contained in an amount of the range of 0.05 to 500 mg, 0.05 to 450 mg, 0.05 to 400 mg, 0.05 to 350 mg, 0.05 to 300 mg, 0.05 to 250 mg, 0.1 to 500 mg, 0.1 to 450 mg, 0.1 to 400 mg, 0.1 to 350 mg, 0.1 to 300 mg, 0.1 to 250 mg, 0.1 to 200 mg, 0.2 to 500 mg, 0.2 to 400 mg, 0.2 to 300 mg, 0.5 to 300 mg, 1 to 300 mg, 5 to 300 mg, or 10 to 300 mg.

In addition, when the composition is used pharmaceutically, the composition may be administered in a pharmaceutically effective amount. In the present invention, a "pharmaceutically effective amount" means an amount sufficient to treat a disease with a reasonable benefit/risk ratio applicable to medical treatment, and an effective dose level may be determined based on the type and severity of the patient's disease, the activity of the pharmaceuticals, sensitivity to the pharmaceuticals, time of administration, route of administration and rate of elimination, duration of treatment, factors including the concurrently used pharmaceuticals, and other factors well known in the medical field. The effective dose is generally 0.01 to 5000 mg per 1 kg of body weight per day, and may be administered in divided doses, such as, but is not limited to, once daily or several times daily at regular time intervals, as determined by a physician or pharmacist. The composition may be administered as an individual therapeutic agent, or in combination with other therapeutic agents, and may be administered concurrently, separately, or sequentially with conventional therapeutic agents, and may be administered in single or multiple doses. It is important to take all of the above factors into account and administer an amount that achieves the maximum effect in the least amount without side effects, which can be readily determined by one of ordinary skill in the art. Specifically, the effective amount of the composition may vary depending on the patient's age, gender, condition, weight, absorption of the active ingredient in the body, rate of inactivation, rate of excretion, type of disease, concurrent pharmaceuticals, and may increase or decrease depending on the route of administration, severity of obesity, gender, weight, age, and the like, and may vary depending on the severity of the state being treated. As necessary, the total daily dose may be divided into multiple doses throughout the day for convenience. In an example, the daily dose may be from approximately 0.0001 mg/kg to approximately 10 g/kg per day, for example, an amount from approximately 0.001 mg/kg to approximately 1 g/kg per day, may be administered once daily. Further, the duration of administration may be from one day to two months, but may be administered without limitation until the effect of preventing or treating the disease is achieved. In addition, the composition may be administered in divided doses several times daily at regular time intervals, for example, two to three times daily, as determined by the physician or pharmacist.

In addition, it is still another aspect of the present invention to provide a method of inducing the secretion of a protein expressed in an intestinal microorganism outside a cell. The method includes a step of administering a recombinant microorganism transformed with the vector that includes a polynucleotide encoding a signal sequence capable of inducing a protein to be secreted outside the cell. The microorganism may be administered in the form of the composition described above.

In addition, it is yet another aspect of the present invention to provide a use of a recombinant microorganism transformed with the vector, for inducing the secretion of a secretion targeted protein outside a cell.

Hereinafter, the present invention will be described in detail through experimental examples.

However, the following experimental examples are specifically illustrative of the present invention, and the contents of the present invention are not limited by the following embodiments.

Experimental Example 1

Confirmation of Effect of Inducing Protein Secretion in *E. coli* Nissle Strain of Signal Sequence of the Present Invention The *Escherichia coli* Nissle strain, which is known to be viable in the intestine and to have an activity that is beneficial to various diseases and health of the human body, was transformed after fusing the signal sequence of the present invention with a foreign protein, and it was confirmed whether the secretion of the foreign protein outside the cell of the *E. coli* Nissle strain was successfully achieved.

Specifically, the polynucleotide encoding the signal sequences of SEQ ID NO: 3, SEQ ID NO: 4, and SEQ ID NO: 5 was operably linked to an upstream portion of a gene sequence encoding an Amuc1102 protein, an Amuc1409 protein, or a fusion protein (Amuc1102+Amuc1409) of the Amuc1102 and Amuc1409 that are derived from *Akkermansia muciniphila*. The fusion protein of Amuc1102 and Amuc1409 described above was designed to be expressed in a linked form with a linker sequence of 5'-GGGGS-3'. The vector was manufactured by inserting the foreign protein gene into the pET-22b(+) vector and linking the polynucleotide encoding the signal sequence of the present invention to the upstream thereof and the sequence encoding the His6 tag to the downstream thereof. Then, the *Escherichia coli* Nissle 1917 strain obtained from Pharma Zentrale GmbH was transformed by electroporation with the vector above and cultured in LB at a temperature of 18° C. or 37° C. for 16 hours. IPTG was added to the culture solution to induce the expression of the protein inserted into the vector, and then at an occasion in which 4 hours or 24 hours had elapsed, a sample of the culture solution was taken and centrifuged under the conditions of 3,000 rpm, 20 minutes, 4° C., and the settled cell and supernatant were obtained. The supernatant was filtered and the protein was obtained by TCA precipitation at a temperature of −20° C. The settled cell was crushed using a sonicator (Sonics & Materials, 4 s on, 4 s off, and 26% amplitude conditions) to obtain a total fraction, and then a portion thereof was centrifuged under conditions of 14,000 rpm, 20 min, and 4° C. to separate the supernatant into a soluble fraction and the settled pellet into an insoluble fraction. The samples obtained as above were subjected to SDS-PAGE and western blotting to separate the protein and detect the presence and amount of the Amuc1102 protein (28.07 kDa), the Amuc1409 protein (17.80 kDa), the fusion protein (43.7 kDa) of Amuc1409 and Amuc1409, and the fusion protein (29.5 kDa) of YebF and Amuc1409.

Figure 2:
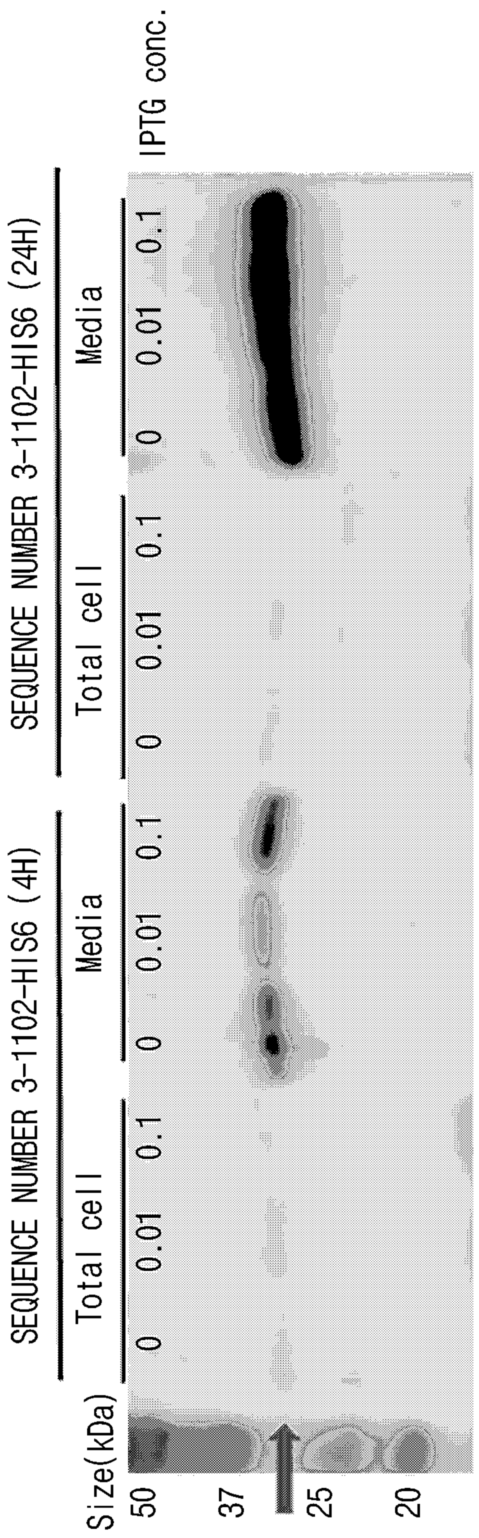
FIG. 2 illustrates western blotting results performed after 4 hours and 24 hours has elapsed following expression of Amuc1102 protein of a linked form of a signal sequence of SEQ ID NO: 3 in *E. coli* Nissle 1917 strain.

As a result, the Amuc1102 protein linked to the signal sequence of SEQ ID NO: 3 of the present invention was confirmed to be present in the culture solution as well as in the cellular lysate of the Nissle 1917 strain, and it was confirmed that the amount of extracellular Amuc1102 protein measured after inducing the protein expression for 4 hours was greater than the amount of Amuc1102 protein measured after inducing the protein expression for 24 hours (FIG. 2). Therefore, it was confirmed that the Amuc1102 protein was secreted and transported outside the *E. coli* cell as the Amuc1102 protein was expressed in linkage with the signal sequence of SEQ ID NO: 3 of the present invention.

Figure 3:
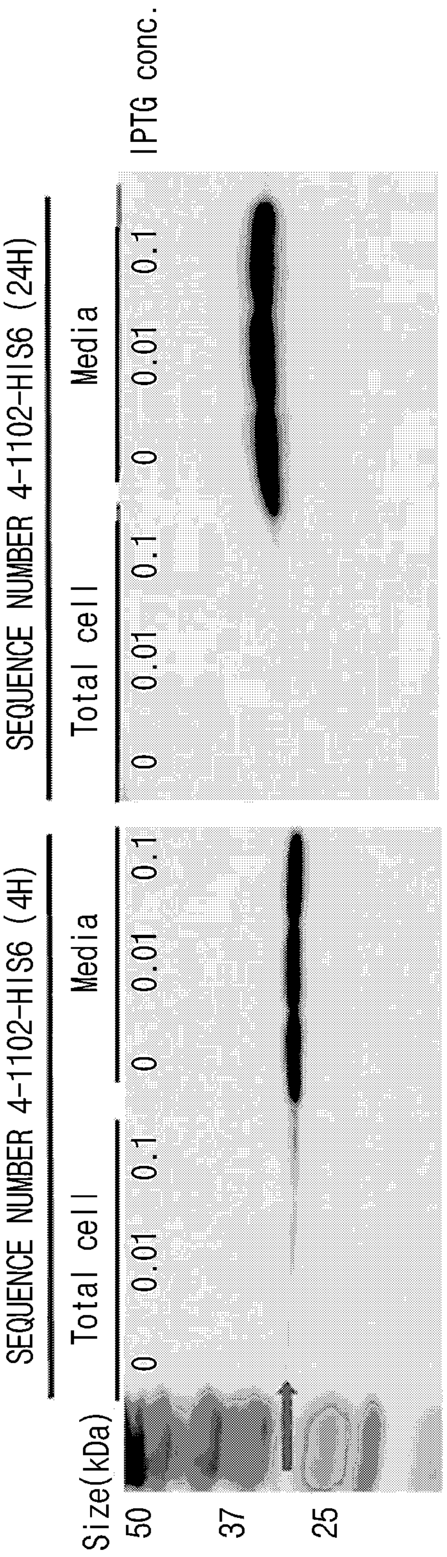
FIG. 3 illustrates western blotting results after 4 hours and 24 hours has elapsed following expression of the Amuc1102 protein linked to a signal sequence of SEQ ID NO: 4 in *E. coli* Nissle 1917 strain.
Figure 4:
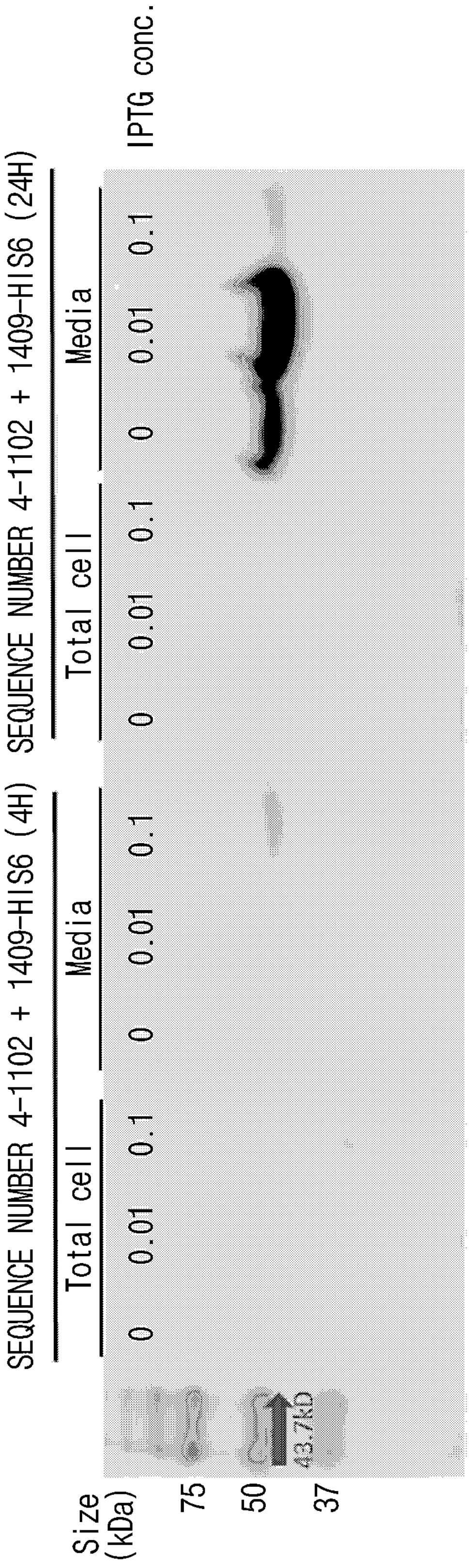
FIG. 4 illustrates western blotting results after 4 hours and 24 hours has elapsed following expression of a fusion protein of Amuc1102 and Amuc1409 linked to a signal sequence of SEQ ID NO: 4 in *E. coli* Nissle 1917 strain.
Figure 5:
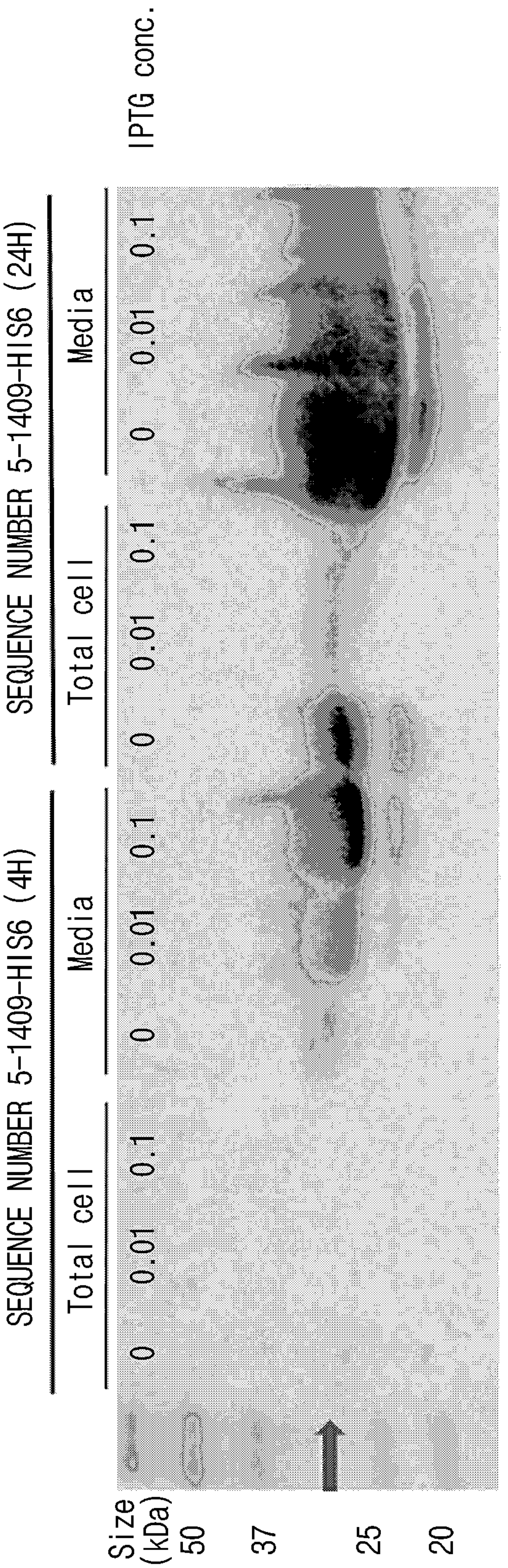
FIG. 5 illustrates western blotting results after 4 hours and 24 hours has elapsed following expression of Amuc1409 protein linked to a protein of SEQ ID NO: 5 in *E. coli* Nissle 1917 strain.
Figure 6:
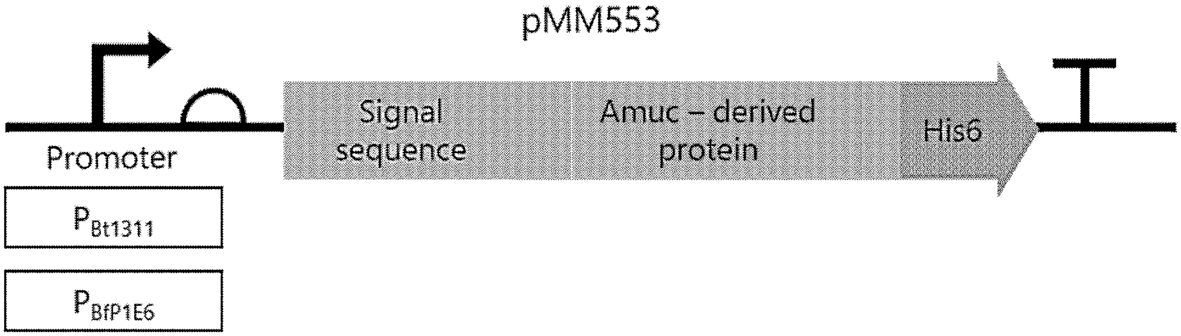
FIG. 6 is a view illustrating a configuration of a vector for transformation of *Bacteroides thetaiotaomicron* strain, in which the vector includes a polynucleotide encoding a protein derived from *Akkermansia muciniphila*, a polynucleotide encoding a His6 tag, and a polynucleotide encoding a signal sequence peptide. In addition, the vector includes a $P_{BT1311}$ promoter or a $P_{BfP1E6}$ promoter.

In addition, the Amuc1102 protein linked to the signal sequence of SEQ ID NO: 4, or the fusion protein of Amuc1102 and Amuc1409 linked to the signal sequence of SEQ ID NO: 4, were also confirmed to be present outside the cell at an occasion in which 4 hours and 24 hours had elapsed after expression (FIGS. 3 and 4), and thus confirming that the proteins were successfully secreted outside the *E. coli* Nissle 1917 strain by the signal sequence of SEQ ID NO: 4. Further, even when the sequence of SEQ ID NO: 5 was used, it was confirmed that the Amuc1409 protein and the protein of SEQ ID NO: 5 were present outside the cell in a fused form (FIG. 5), thus confirming that it was possible to induce external secretion of the foreign protein in the *E. coli* Nissle 1917 strain.

In view of the above results, it was confirmed that the signal sequences of SEQ ID NO: 3, SEQ ID NO: 4, and SEQ ID NO: 5 of the present invention can induce the external secretion of foreign protein in the *E. coli* Nissle 1917 strain, which is a type of probiotic that can grow in the intestine and is beneficial to the human body, and thus confirming that the signal sequences above can be usefully used to express and secrete the protein in the intestine, which can help improve the health of humans or animals or ameliorate diseases.

Experimental Example 2

Confirmation of Effect of Inducing Protein Secretion in *Bacteroides thetaiotaomicron* Strain of Signal Sequence of the Present Invention The *Bacteroides thetaiotaomicron* strain, which is a dominant microorganism in the intestine and is known to provide beneficial assistance to the human body, was transformed after fusion of the signal sequence of the present invention with a foreign protein to confirm whether the foreign protein is successfully secreted outside the cell of the *Bacteroides thetaiotaomicron* strain.

Specifically, the polynucleotide encoding the signal sequences of SEQ ID NO: 1, SEQ ID NO: 2, and SEQ ID NO: 3 was operably linked to an upstream portion of a gene sequence encoding an Amuc1102 protein, an Amuc1409 protein, or a fusion protein (Amuc1102+Amuc1409) of the Amuc1102 and Amuc1409 that are derived from *Akkermansia muciniphila*. The fusion protein of Amuc1102 and Amuc1409 described above was designed to be expressed in a linked form with a linker sequence of 5'-GGGGS-3'. The vector was manufactured by inserting the foreign protein gene into the pMM553 vector and linking the polynucleotide encoding the signal sequence of the present invention to the upstream thereof and the sequence encoding the His6 tag to the downstream thereof. In addition, a promoter was operably linked to the encoding sequences in the above vector, in which the promoter used was the $P_{BT1311}$ promoter from *Bacteroides thetaiotaomicron* or the *Bacteroides fragilis*-infecting phage-derived $P_{BfP1E6}$ promoter, respectively. Further, the *Bacteroides thetaiotaomicron* strain obtained from the Korean Collection for Type Culture was transformed into the vector above. For transformation, the *E. coli* WM3064, which can function as a donor cell, was first transformed with the vector and cultured in LB, while the wild-type of *Bacteroides thetaiotaomicron* strain was cultured in BHIS. When the O.D. of both strains reached 0.2 to 0.3, 0.2 ml of *E. coli* WM3064 and 1.4 ml of *Bacteroides thetaiotaomicron* each were transferred to a 1.5 ml tube, centrifuged at 7,200 g for 2 minutes, discarded the supernatant, and centrifuged again with 0.2 ml of BHIS added under the same conditions. The supernatant was discarded again and 20 μl of BHIS was used to mix the strains of *E. coli* WM3064 and *Bacteroides thetaiotaomicron*. Then, a sterilized circular filter of 0.22 μm was placed on a BHIS+5% sheep blood plate, and the culture solution of the *E. coli* and *Bacteroides* above was inoculated thereon. The filter was dried until the culture solution was completely absorbed, then incubated aerobically at 37° C. for 20 hours, after which the filter was obtained and put into 5 ml of PBS and vortex-mixed. Then, 0.2 ml of the culture solution was smeared on a BHIS+Erythromycin (25 μg/ml) plate and anaerobically cultured for 2 to 3 days to obtain the *Bacteroides thetaiotaomicron* strain transformed with the vector. After expressing the protein inserted into the vector, a sample of the culture solution was taken at an occasion in which 24 hours had elapsed and centrifuged at 3,000 rpm, 20 minutes, 4° C., and the settled cell and supernatant were obtained. The supernatant was filtered and the protein was obtained by TCA precipitation at a temperature of −20° C. The settled cell was crushed using a sonicator (Sonics & Materials, 4 s on, 4 s off, and 26% amplitude conditions). The samples obtained as above were subjected to SDS-PAGE and western blotting to separate the protein and detect the presence and amount of the Amuc1102 protein (28.07 kDa), the Amuc1409 protein (17.80 kDa), the fusion protein (43.7 kDa) of Amuc1409 and Amuc1409.

Figure 7:
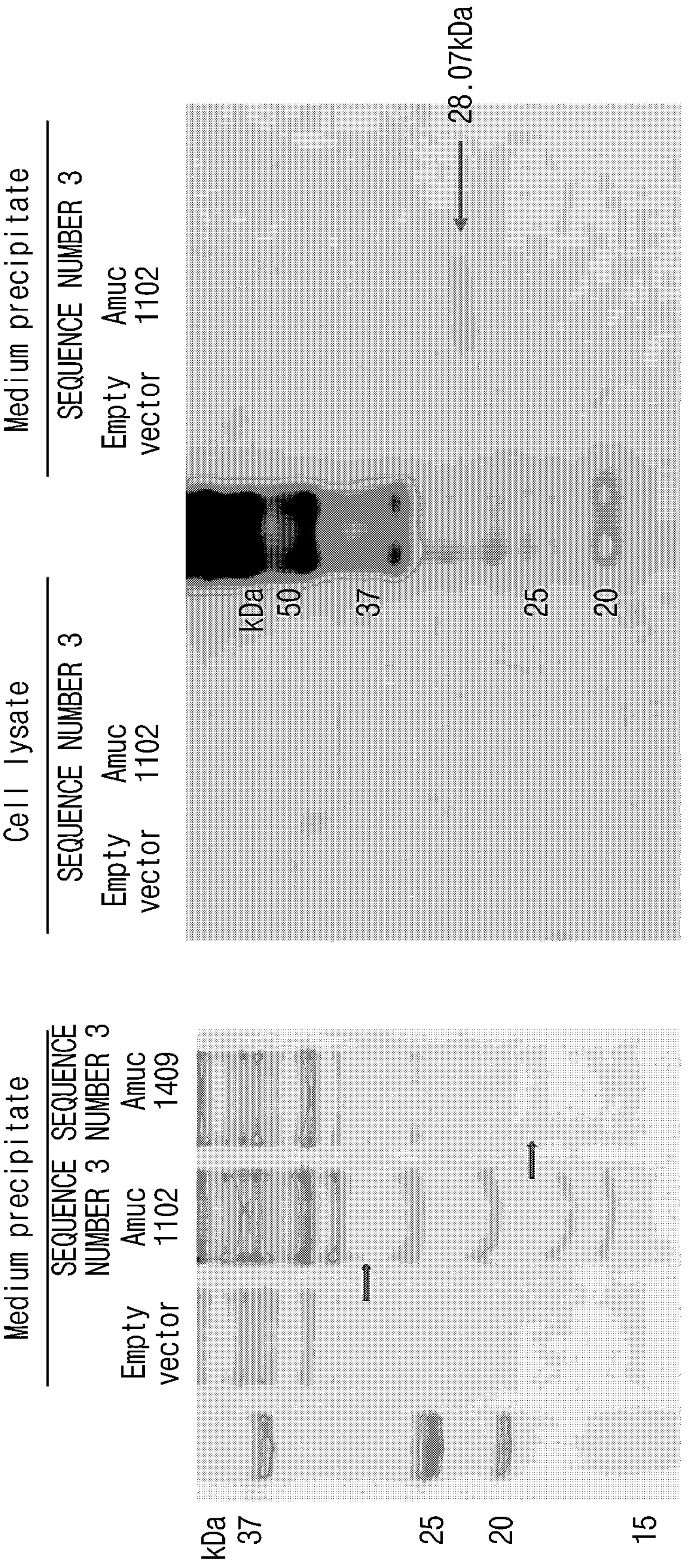
FIG. 7 illustrates SDS-PAGE results (left) and western blotting results (right) performed after 24 hours has elapsed following linkage of a signal sequence of SEQ ID NO: 3 to the Amuc1102 protein and Amuc1409 protein, respectively and expression thereof in a *Bacteroides thetaiotaomicron* strain using the $P_{BT1311}$ promoter.

As a result, the Amuc1102 protein linked to the signal sequence of SEQ ID NO: 3 of the present invention expressed using the $P_{BT1311}$ promoter, and the Amuc1409 protein linked to the signal sequence of SEQ ID NO: 3 of the present invention were confirmed to be present in the culture solution as well as in the cell lysate of the *Bacteroides thetaiotaomicron* strain (FIG. 7).

Therefore, it was confirmed that the Amuc1102 protein and Amuc1409 protein was secreted and transported outside the cell as the Amuc1102 protein and Amuc1409 protein was expressed in linkage with the signal sequence of SEQ ID NO: 3 of the present invention.

Figure 8:
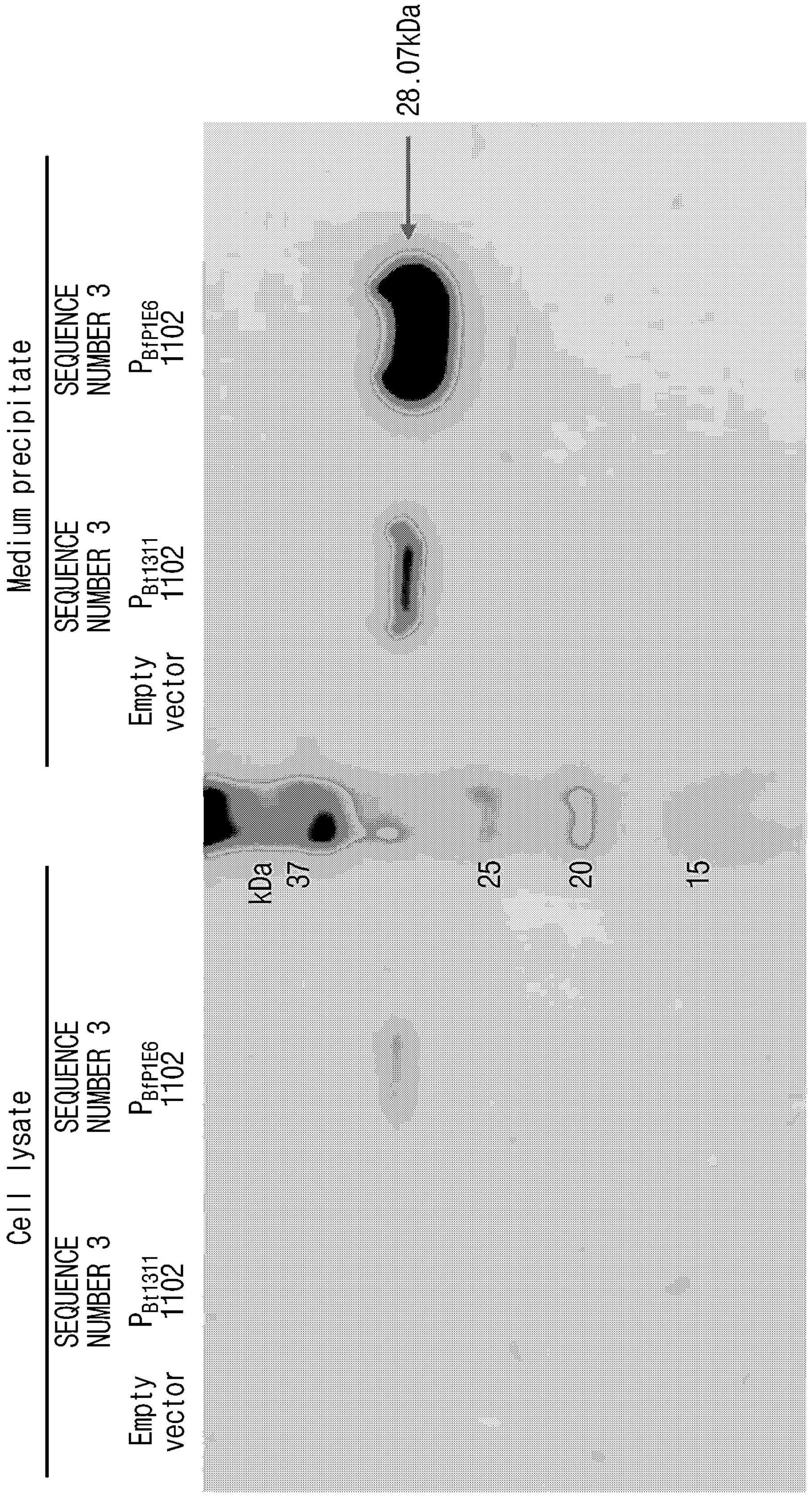
FIG. 8 illustrates western blotting results performed following linkage of a signal sequence of SEQ ID NO: 3 to the Amuc1102 protein and expression thereof in the *Bacteroides thetaiotaomicron* strain using the $P_{BT1311}$ promoter or the $P_{BfP1E6}$ promoter.

In addition, when the signal sequence of SEQ ID NO: 3 of the present invention and the gene sequence of the Amuc1102 protein were expressed using the $P_{BfP1E6}$ promoter, it was confirmed that the extracellular secretion of the Amuc1102 protein successfully occurred, and the expression and the amount of secretion were further increased when compared to the expression using the $P_{BT1311}$ promoter (FIG. 8).

Figure 9:
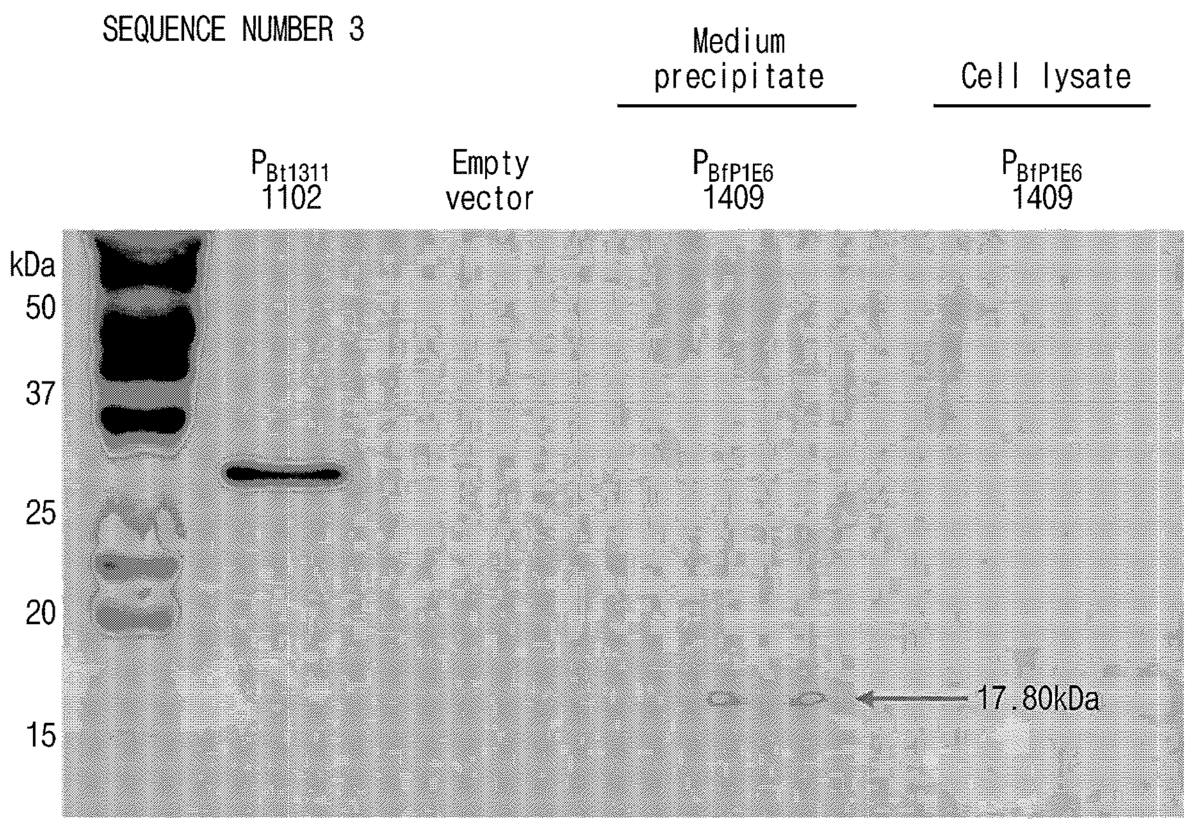
FIG. 9 illustrates western blotting results performed following linkage of a signal sequence of SEQ ID NO: 3 to the Amuc1409 protein and expression thereof in the *Bacteroides thetaiotaomicron* strain using the $P_{BfP1E6}$ promoter.
Figure 10:
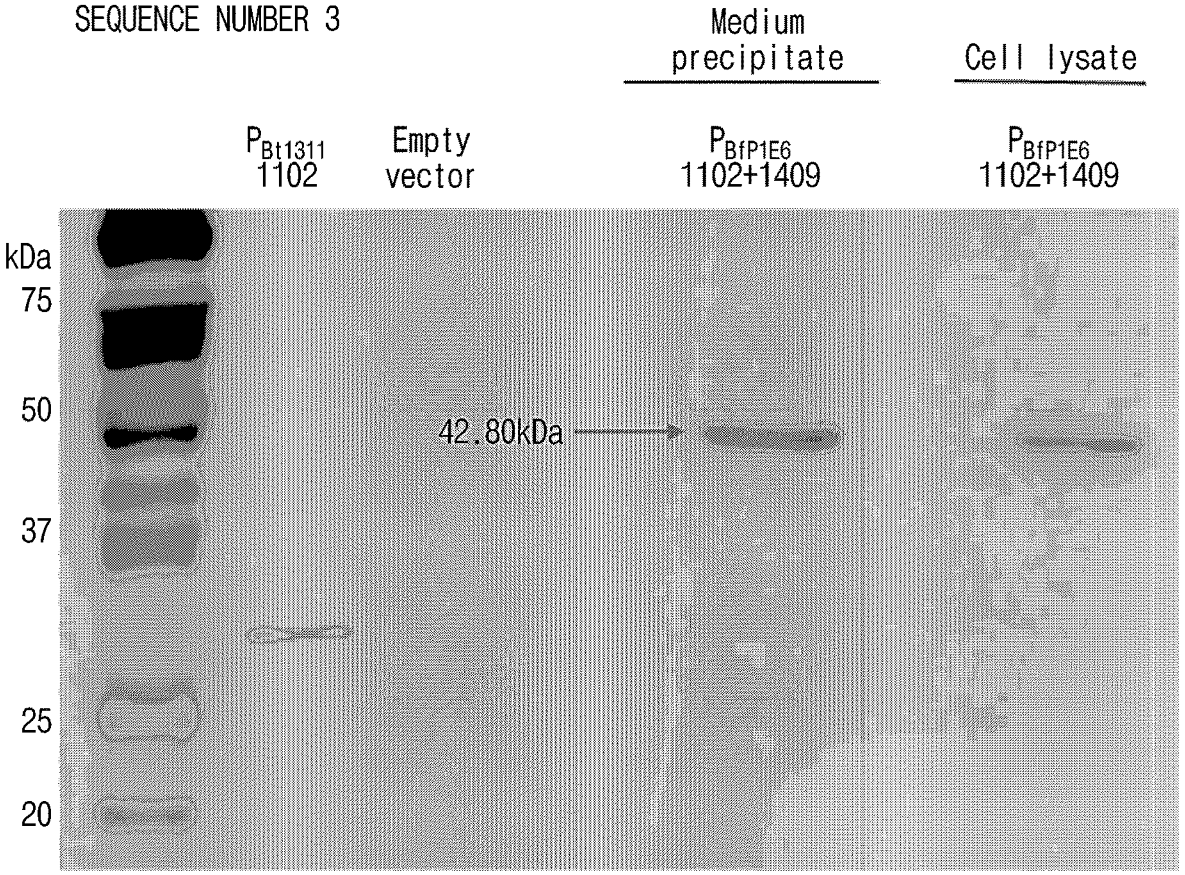
FIG. 10 illustrates western blotting results performed following linkage of a signal sequence of SEQ ID NO: 3 to a fusion protein of Amuc1102 and Amuc1409 and expression thereof in the *Bacteroides thetaiotaomicron* strain using the $P_{BfP1E6}$ promoter.

It was confirmed that the signal sequence of SEQ ID NO: 3 induced the extracellular secretion of Amuc1409 protein even when linked to the Amuc1409 protein. As can be seen in FIG. 9, the western blotting results showed that a band of Amuc1409 was observed after the $P_{BfP1E6}$ promoter, the polynucleotide encoding the signal sequence of SEQ ID NO: 3, and the Amuc1409 protein gene were linked and expressed. Further, it was confirmed that the signal sequence of SEQ ID NO: 3 was capable of inducing extracellular secretion even for the fusion protein of Amuc1102 and Amuc1409 when the $P_{BfP1E6}$ promoter was used (FIG. 10).

Figure 11:
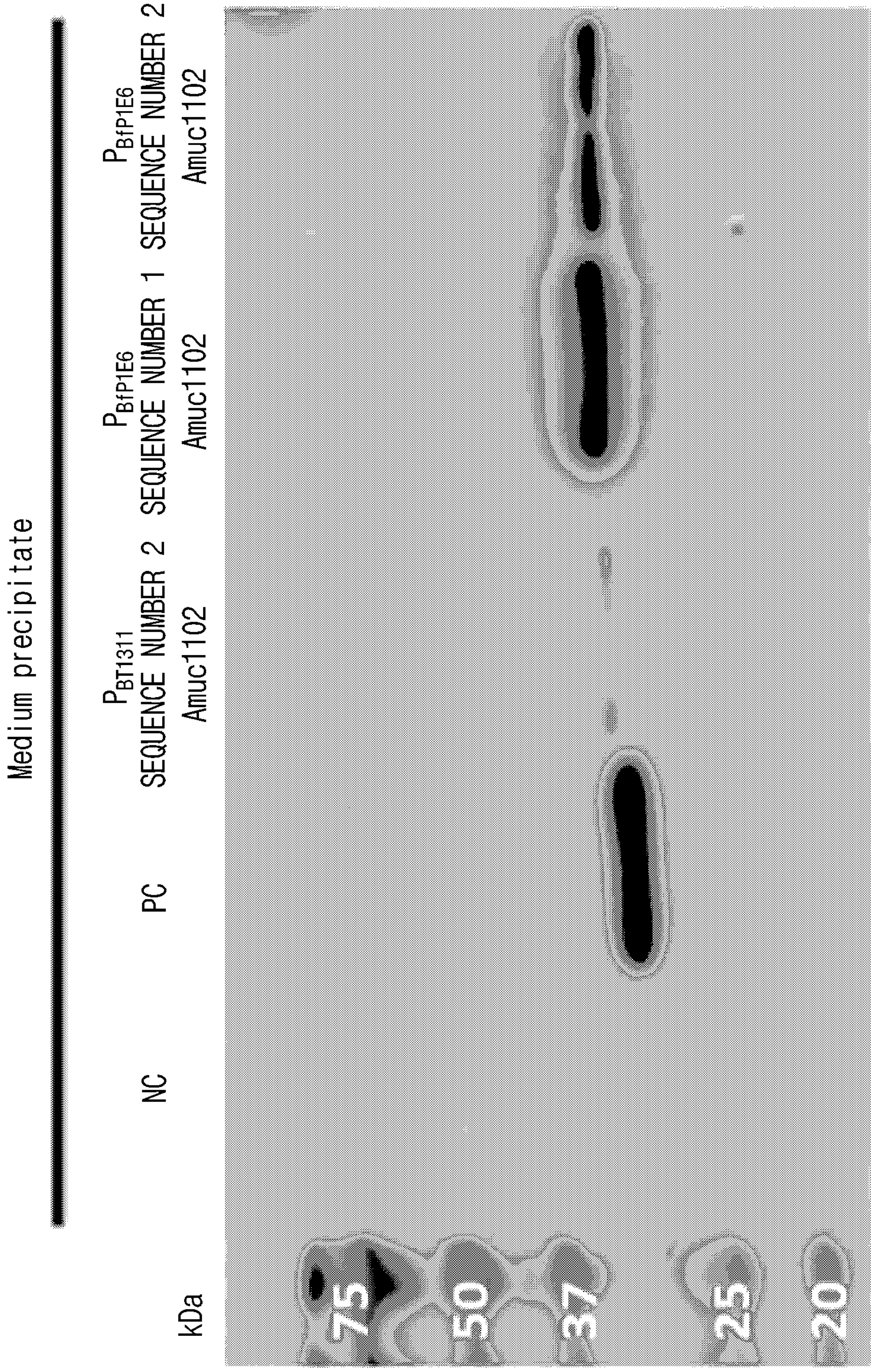
FIG. 11 illustrates western blotting results performed following linkage of a signal sequence of SEQ ID NO: 2 to the Amuc1102 protein and expression thereof in the *Bacteroides thetaiotaomicron* strain using the $P_{BT1311}$ promoter, and western blotting results performed following linkage of a signal sequence of SEQ ID NO: 1 or SEQ ID NO: 2 to the Amuc1102 protein and expression thereof in the *Bacteroides thetaiotaomicron* strain using the $P_{BfP1E6}$ promoter.

Furthermore, it was confirmed that the signal sequences of SEQ ID NO: 1 and SEQ ID NO: 2 of the present invention were capable of inducing extracellular secretion of the foreign protein in *Bacteroides thetaiotaomicron* strain. Specifically, when the Amuc1102 protein linked to SEQ ID NO: 2 was expressed using the $P_{BT1311}$ promoter, the secretion thereof was confirmed, and when the Amuc1102 protein linked to SEQ ID NO: 1 or SEQ ID NO: 2, respectively, was expressed using the $P_{BfP1E6}$ promoter, the secretion thereof outside the cell was confirmed (FIG. 11).

In view of the above results, it was confirmed that the signal sequences of SEQ ID NO: 1, SEQ ID NO: 2, and SEQ ID NO: 3 of the present invention can induce the external secretion of foreign protein in the *Bacteroides thetaiotaomicron* strain, which is a type of probiotic that can grow in the intestine and is beneficial to the human body, and thus confirming that the signal sequences above can be usefully used to express and secrete the protein in the intestine, which can help improve the health of humans or animals or ameliorate diseases.

Although representative experimental examples of the present invention have been described above as illustrative, the scope of the present invention is not limited to the specific experimental examples described above, and those of ordinary skill in the art will be able to make appropriate modifications within the scope of the claims of the present invention.

The invention claimed is:

1. A fusion protein comprising: i) a signal sequence peptide including one selected from the group consisting of amino acid sequences of SEQ ID NO: 1, SEQ ID NO: 2, and SEQ ID NO: 3; and ii) a target protein heterologous to the signal sequence, wherein the target protein is configured to be secreted extracellularly.

2. The fusion protein of claim 1, wherein the fusion protein is expressed in a host cell of *Escherichia coli* or *Bacteroides* genus, and wherein the target protein is secreted extracellularly.

3. A vector comprising a polynucleotide encoding the fusion protein of claim 1, wherein the vector is configured to express the fusion protein.

4. The vector of claim 3, wherein the vector is configured to express the fusion protein in a microbial strain viable in the intestine, and wherein the signal sequence directs secretion of the target protein extracellularly.

5. The vector of claim 4, wherein the microbial strain viable in the intestine is a microbial strain of *Escherichia coli* or *Bacteroides* genus.

6. The vector of claim 5, wherein the *E. coli* is a *E. coli* Nissle 1917 strain.

7. The vector of claim 5, wherein the microbial strain of *Bacteroides* genus is a *Bacteroides thetaiotaomicron* strain.

8. The vector of claim 3, further comprising a promoter operably linked to the polynucleotide.

9. The vector of claim 8, wherein the promoter is a *Bacteroides thetaiotaomicron*-derived BT1311 promoter ($P_{BT1311}$) or a *Bacteroides fragilis*-infecting phage-derived BfP1E6 promoter ($P_{BfP1E6}$).

10. A recombinant microorganism transformed with the vector of claim 3.

11. A method of manufacturing a target protein, comprising:

culturing the recombinant microorganism of claim 10 under conditions that allow expression of the fusion protein; and recovering the target protein secreted extracellularly.

12. A composition comprising the recombinant microorganism of claim 10; and a cryoprotectant.

13. The composition of claim 12, wherein the recombinant microorganism is a microorganism that is viable in the intestine.

14. The composition of claim 12, wherein the composition is configured to express the target protein in the intestine.

15. The composition of claim 12, wherein the composition is a health functional food composition.

* * * * *

SEQUENCE LISTING

```
<160> NUMBER OF SEQ ID NOS: 10

<210> SEQ ID NO 1
<211> LENGTH: 25
<212> TYPE: PRT
<213> ORGANISM: Artificial Sequence
<220> FEATURE:
<223> OTHER INFORMATION: Bt3742 amino acid sequence

<400> SEQUENCE: 1

Met Lys Ile Met Lys Lys Arg Leu Leu Tyr Leu Phe Met Leu Ile Cys
```

```
1               5                   10                  15

Ser Ile Ser Leu Phe Val Ser Cys Ser
            20                  25


<210> SEQ ID NO 2
<211> LENGTH: 23
<212> TYPE: PRT
<213> ORGANISM: Artificial Sequence
<220> FEATURE:
<223> OTHER INFORMATION: Bt4368 amino acid sequence

<400> SEQUENCE: 2

Met Lys Ile Lys Thr Leu Val Ala Met Leu Phe Leu Ser Ala Gly Ala
1               5                   10                  15

Thr Thr Val Val Ala Gln Asp
            20


<210> SEQ ID NO 3
<211> LENGTH: 24
<212> TYPE: PRT
<213> ORGANISM: Artificial Sequence
<220> FEATURE:
<223> OTHER INFORMATION: 1102ss amino acid sequence

<400> SEQUENCE: 3

Met Lys Ser Ile Leu Asn Thr Ile Thr Ala Met Leu Ala Ala Val Leu
1               5                   10                  15

Phe Val Pro Ala Ala Ser Ala Gln
            20


<210> SEQ ID NO 4
<211> LENGTH: 22
<212> TYPE: PRT
<213> ORGANISM: Artificial Sequence
<220> FEATURE:
<223> OTHER INFORMATION: pelB amino acid sequence

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala
            20


<210> SEQ ID NO 5
<211> LENGTH: 118
<212> TYPE: PRT
<213> ORGANISM: Artificial Sequence
<220> FEATURE:
<223> OTHER INFORMATION: YebF amino acid sequence

<400> SEQUENCE: 5

Met Lys Lys Arg Gly Ala Phe Leu Gly Leu Leu Leu Val Ser Ala Cys
1               5                   10                  15

Ala Ser Val Phe Ala Ala Asn Asn Glu Thr Ser Lys Ser Val Thr Phe
            20                  25                  30

Pro Lys Cys Glu Asp Leu Asp Ala Ala Gly Ile Ala Ala Ser Val Lys
        35                  40                  45

Arg Asp Tyr Gln Gln Asn Arg Val Ala Arg Trp Ala Asp Asp Gln Lys
    50                  55                  60

Ile Val Gly Gln Ala Asp Pro Val Ala Trp Val Ser Leu Gln Asp Ile
65                  70                  75                  80

Gln Gly Lys Asp Asp Lys Trp Ser Val Pro Leu Thr Val Arg Gly Lys
```

```
                85                  90                  95

Ser Ala Asp Ile His Tyr Gln Val Ser Val Asp Cys Lys Ala Gly Met
            100                 105                 110

Ala Glu Tyr Gln Arg Arg
        115


<210> SEQ ID NO 6
<211> LENGTH: 75
<212> TYPE: DNA
<213> ORGANISM: Artificial Sequence
<220> FEATURE:
<223> OTHER INFORMATION: Bt3742 DNA sequence

<400> SEQUENCE: 6

atgaagatta tgaagaaaag attgttgtat ttgttcatgc ttatttgttc cataagttta     60

tttgtgagtt gtagt                                                      75


<210> SEQ ID NO 7
<211> LENGTH: 69
<212> TYPE: DNA
<213> ORGANISM: Artificial Sequence
<220> FEATURE:
<223> OTHER INFORMATION: Bt4368 DNA sequence

<400> SEQUENCE: 7

atgaaaatta aaacgcttgt ggctatgttg ttcctttcgg ctggagcaac cactgtggtg     60

gcacaggat                                                             69


<210> SEQ ID NO 8
<211> LENGTH: 72
<212> TYPE: DNA
<213> ORGANISM: Artificial Sequence
<220> FEATURE:
<223> OTHER INFORMATION: 1102ss DNA sequence

<400> SEQUENCE: 8

atgaagtcaa tccttaacac aatcacagct atgcttgcgg ctgttctgtt cgtaccggct     60

gcatctgccc ag                                                         72


<210> SEQ ID NO 9
<211> LENGTH: 66
<212> TYPE: DNA
<213> ORGANISM: Artificial Sequence
<220> FEATURE:
<223> OTHER INFORMATION: pelB DNA sequence

<400> SEQUENCE: 9

atgaaatacc tgctgccgac cgctgctgct ggtctgctgc tcctcgctgc ccagccggcg     60

atggcc                                                                66


<210> SEQ ID NO 10
<211> LENGTH: 354
<212> TYPE: DNA
<213> ORGANISM: Artificial Sequence
<220> FEATURE:
<223> OTHER INFORMATION: YebF DNA sequence

<400> SEQUENCE: 10

atgaaaaaaa gaggggcgtt tttagggctg ttgttggttt ctgcctgcgc atcagttttc     60

gctgccaata atgaaaccag caagtcggtc actttcccaa agtgtgaaga tctggatgct    120

gccggaattg ccgcgagcgt aaaacgtgat tatcaacaaa atcgcgtggc gcgttgggca    180
```

-continued

| | |
|---|---|
| gatgatcaaa aaattgtcgg tcaggccgat cccgtggctt gggtcagttt gcaggacatt | 240 |
| cagggtaaag atgataaatg gtcagtaccg ctaaccgtgc gtggtaaaag tgccgatatt | 300 |
| cattaccagg tcagcgtgga ctgcaaagcg ggaatggcgg aatatcagcg gcgt | 354 |